United States Patent
Mikoshiba et al.

(10) Patent No.: US 9,314,501 B2
(45) Date of Patent: Apr. 19, 2016

(54) METHOD OF REGULATING NEURONAL AXON ELONGATION

(71) Applicant: RIKEN, Saitama (JP)

(72) Inventors: Katsuhiko Mikoshiba, Saitama (JP); Hiroyuki Kabayama, Saitama (JP)

(73) Assignee: RIKEN, Saitama (JP)

( * ) Notice: Subject to any disclaimer, the term of this patent is extended or adjusted under 35 U.S.C. 154(b) by 128 days.

(21) Appl. No.: 13/869,116

(22) Filed: Apr. 24, 2013

(65) Prior Publication Data

US 2013/0288977 A1    Oct. 31, 2013

Related U.S. Application Data

(60) Provisional application No. 61/638,772, filed on Apr. 26, 2012.

(51) Int. Cl.

| | |
|---|---|
| *A61K 31/70* | (2006.01) |
| *A61K 38/00* | (2006.01) |
| *C07H 21/04* | (2006.01) |
| *A61K 38/17* | (2006.01) |
| *A61K 31/4965* | (2006.01) |
| *G01N 33/50* | (2006.01) |
| *A61K 48/00* | (2006.01) |

(52) U.S. Cl.
CPC ............ *A61K 38/177* (2013.01); *A61K 31/4965* (2013.01); *G01N 33/5058* (2013.01); *A61K 48/00* (2013.01); *A61K 48/005* (2013.01); *C07H 21/04* (2013.01)

(58) Field of Classification Search
CPC ....... A61K 48/00; A61K 48/005; C07H 21/04
USPC ...................... 514/44 R, 17.7; 536/23.5, 24.1
See application file for complete search history.

(56) References Cited

PUBLICATIONS

Gorecki, D., 2001, Expert Opin. Emerging Drugs, 6(2): 187-198.*
Bennett, J., 2003, Gene Therapy, vol. 10, p. 977-982.*
Thomas et al., 2003, Nature Reviews/ Genetics, vol. 4, p. 346-358.*
Kodama et al., 2006, Current Medicinal Chemistry, vol. 13, p. 2155-2161.*
Takahashi et al., 2012, Frontiers in Bioscience, vol. S4, p. 133-141.*
Kaur et al., 2009, Current Gene Therapy, vol. 9. p. 434-458.*
Castro et al., 2001, Histl. Histopathol., vol. 16, p. 1225-1238.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002 Virology, vol. 304, p. 135-145.*
Chattopadhyay et al., 2004, Virus Research, vol. 99, p. 139-145.*
Fournier et al., "Semaphorin3A Enhances Endocytosis at Sites of Receptor-F-actin Colocalization during Growth Cone Collapse", The Journal of Cell Biology, vol. 149, No. 2, Apr. 17, 2000, p. 411-421.
Jurney et al., "Rac1-Mediated Endocytosis during Ephrin-A2-and Semaphorin3A-Induced Growth Cone Collapse", The Journal of Neuroscience, Jul. 15, 2002, p. 6019-6028.
Mercer et al., "Virus entry by macropinocytosis", Nature Cell Biology, vol. 11, No. 5, May 2009, p. 510-520.
Mikule et al., "Growth Cone Collapse Induced by Semaphorin 3A Requires 12/15-Lipoxygenase", The Journal of Neuroscience, Jun. 15, 2002, p. 4932-4941.
Piper et al., "Endocytosis-dependent desensitization and protein synthesis-dependent resensitization in retinal growth cone adaptation", Nat Neurosci. Feb. 2005, p. 1-19.
Swanson et al., "Macropinocytosis", Trends in Cell Biology, vol. 5, Nov. 1995, p. 424-428.
Wadia et al., "Transducible TAT-HA fusogenic peptide enhances escape of TAT-fusion proteins after lipid raft macropinocytosis", Nature Medicine, vol. 10, No. 3, Mar. 2004, p. 310-315.
Wadia et al., "Pathologic Prion Protein Infects Cells by Lipid-Raft Dependent Macropinocytosis", Oct. 2008, vol. 3, Issue 10, p. 1-8.

\* cited by examiner

*Primary Examiner* — Shin Lin Chen (74) *Attorney, Agent, or Firm* — Renner, Otto, Boisselle & Sklar, LLP (57) ABSTRACT

The present invention includes a treating step of treating neuronal growth cone with a regulatory factor to regulate macropinocytosis caused by a repulsive axon guidance molecule. The present invention can provide a new neuronal axon elongation regulating method etc.

2 Claims, 8 Drawing Sheets

METHOD OF REGULATING NEURONAL AXON ELONGATION

CROSS-REFERENCE TO RELATED APPLICATIONS

This Nonprovisional application claims benefit on U.S. Provisional Application Ser. No. 61/638,722 filed on Apr. 26, 2012, the entire contents of which are hereby incorporated by reference.

TECHNICAL FIELD

The present invention relates to a new method of regulating neuronal axon elongation.

BACKGROUND ART

As is disclosed in Non-patent literature 1 (p. 136-p. 137), development of neural networks is regulated mainly by action of an attractive axon guidance factor and a repulsive axon guidance factor on a growth cone which is located at the tip of a neurite. The attractive axon guidance factor causes the neurite to grow in a predetermined direction, and the repulsive axon guidance factor causes growth cone collapse, thereby reducing neurite elongation.

Clarification of a detailed mechanism of regulation of development of neural networks would lead to induction of appropriate development of neural networks and induction of regeneration of neural networks. However, many unclear points still remain even in a mechanism of induction of growth cone collapse caused by a repulsive axon guidance factor.

CITATION LIST

Non-Patent Literature
Non-Patent Literature 1
Jikken Igaku (Experimental Medicine) separate volume Bio Science terminology library Cranial Nerves (third edition) (Published on Sep. 1, 1999)

SUMMARY OF INVENTION

Technical Problem

A purpose of the present invention is to provide a method of regulating neuronal axon elongation based on a newly-found mechanism of induction of growth cone collapse caused by a repulsive axon guidance factor, and the like.

Solution to Problem

In order to achieve the above-mentioned purpose, the present invention includes any one of the following features.

A method of regulating neuronal axon elongation, comprising: a treating step of treating neuronal growth cone with a regulatory factor to regulate macropinocytosis caused by a repulsive axon guidance molecule.

A method of screening a regulatory factor for regulating macropinocytosis dependent on a repulsive axon guidance molecule, the method comprising: a culturing step of culturing a neuron in the presence of a candidate of a regulatory factor; a measuring step of measuring binding activity and/or amount of Syntaxin1B protein in a growth cone of the neuron; and a sorting step of sorting the candidate that modulates binding activity and/or amount of Syntaxin1B protein in the growth cone of the neuron as compared with a case where the candidate does not exist.

A neuronal axon elongation regulating agent, comprising: an inhibitor of a sodium/proton exchanger in a growth cone; and a regulatory factor that increases binding activity and/or amount of Syntaxin1B protein in the growth cone.

Advantageous Effects of Invention

The present invention makes it possible to regulate neuronal axon elongation.

DESCRIPTION OF EMBODIMENTS

The embodiment of the present invention is described in detail as follow.

A person skilled in the art appropriately understands that the term "neuronal axon elongation" used herein has the same meaning as the term "nerve-cell growth", and those terms can be replaced with each other.

As used herein, the expression "a treating step of treating a neuronal growth cone with a regulatory factor to regulate macropinocytosis caused by a repulsive axon guidance molecule" has the same meaning as the expression "an acting step of causing a regulatory factor to act on a neuronal growth cone, wherein the regulatory factor regulates repulsive axon guidance molecule-dependent macropinocytosis", and those expressions can be replaced with each other.

[1. Method of Regulating Neuronal Axon Elongation]

(Outline of Method Regulating Neuronal Axon Elongation)

A method of regulating neuronal axon elongation in accordance with the present invention includes a treating step of treating neuronal growth cone with a regulatory factor to regulate macropinocytosis caused by a repulsive axon guidance molecule.

The inventors of the present invention showed for the first time that one part of the mechanism related with the repulsion of neuronal growth cone is macropinocytosis caused by a repulsive axon guidance molecule (see also Example). Further, the inventors found that neuronal axon elongation could be regulated by regulating the macropinocytosis.

Note that the repulsive axon guidance molecule is not limited in kind, and examples of the repulsive axon guidance molecule encompass Sema3A and ephrin-A2, and preferably Sema3A.

(Regulatory Factor)

The regulatory factor regulates macropinocytosis caused by a repulsive axon guidance molecule in a growth cone. Here, the expression "regulating macropinocytosis" means either enhancement or suppression of macropinocytosis as compared with a case where the regulatory factor is absent.

The regulatory factor is not particularly limited in kind, however, preferable examples of the regulatory factor encompass 1) an inhibitor of a sodium/proton exchanger in a growth cone or 2) a factor that modulates binding activity and/or amount of Syntaxin1B protein in a growth cone. Note that "a factor that modulates binding activity and/or amount of Syntaxin1B protein in a growth cone" refers to a factor that increases or decreases the binding activity of Syntaxin1B protein or the amount of Syntaxin1B protein, as compared with a case where the factor is absent. Note that the factor may modulate the binding activity and the amount of Syntaxin1B protein, however, it is preferable that the factor modulate at least the amount of Syntaxin1B protein. The binding activity of Syntaxin1B protein can be determined by measuring binding activity between a biological factor (such as SNAP25, VAMP2, or Synaptotagmin) and Syntaxin1B protein. Note that, in the present specification, "A and/or B" is a concept including both 'A and B' and 'A or B'.

The inhibitor of a sodium/proton exchanger in a growth cone may be any inhibitor that acts as an inhibitor of the sodium/proton exchanger. The examples of the inhibitor of a sodium/proton exchanger in a growth cone encompass Amiloride, EIPA, HMA(5-(N,N-hexamethylene) amiloride), DMA (dimethyl amiloride), HOE-694, Cariporide, Eniporide, Zoniporide, SM20550, BMS-284640, T-162559(S), TY-12533, SL-591227, and S-3226 (Reference Literatures: An overview of inhibitors of Na+/H+ exchanger, Masereel B, Pochet L, and Laechmann D., European Journal of Medicinal Chemistry 38 (2003) 547-554). The inhibitor of the sodium/proton exchanger is preferably 5-(N-ethyl-N-isopropyl) amiloride or an analog thereof such as Amiloride, EIPA, HMA, or DMA, and more preferably 5-(N-ethyl-N-isopropyl)amiloride. These inhibitors suppress occurrence of macropinocytosis and growth cone collapse caused by a repulsive axon guidane molecule, resulting in the cancellation of growth cone collapse of neuron, more specifically growth cone collapse of a neurite. As a result of the cancellation of the growth cone collapse, the neuron can elongate its neurite.

Among factors that modulate binding activity and/or amount of Syntaxin1B protein in a growth cone, a factor that increases binding activity of Syntaxin1B protein and a factor that increases amount of Syntaxin1B protein can suppress (A) occurrence of macropinocytosis in a growth cone caused by a repulsive axon guidance molecule and (B) growth cone collapse. It leads to the cancellation of growth cone collapse of neuron, more specifically growth cone collapse of a neurite. As a result of the cancellation of the growth cone collapse, the neuron can elongate its neurite. Examples of such factors encompass a nucleic acid molecule which encodes Syntaxin1B protein, and Syntaxin1B protein itself. Note that examples of Syntaxin1B protein includes a Syntaxin1B mutant maintaining a function such as binding activity against a target molecule which the wild type Syntaxin1B naturally binds. A Syntaxin1B mutant may have deletion, insertion and/or substitution of approximately 1-10 amino acids, preferably approximately 1-5 amino acids as long as the mutant maintains a function such as binding activity.

Meanwhile, among factors that modulate binding activity and/or amount of Syntaxin1B protein in a growth cone, a factor that decreases binding activity of Syntaxin1B protein and a factor that decreases amount of Syntaxin1B protein induce occurrence of macropinocytosis in a growth cone and growth cone collapse of a neuron (neurite). Examples of such factors encompass (i) nucleic acid molecules such as antisense RNA, shRNA, siRNA, microRNA and the like, each of which has the function to suppress expression of a Syntaxin1B gene, and (ii) artificial nucleic acids whose molecules are equivalent to those of nucleic acids, and each of which has the function to suppress expression of a Syntaxin1B gene.

(Method for Treating Neuron with Regulatory Factor)

A method for treating neuronal growth cone with the above regulatory factor can be appropriately selected in accordance with, for example, a kind of regulatory factor.

In a case where an individual for administration of the regulatory factor is a human or an animal, a regulatory factor is administered to the human or the animal in an amount effective in regulating neuronal axon elongation. Here, the regulatory factor may be administered alone, or may be administered as an ingredient of a pharmaceutical composition (described later) suitable for a purpose of the administration.

A method for administering a regulatory factor is not particularly limited. A regulatory factor may be systemically administered by a method such as oral administration, intravascular administration into a vein or an artery, or enteral administration. Alternatively, a regulatory factor may also be locally administered by a method such as injection (using an injector, or an injection pump), transdermal administration, or sublingual administration. A preferable embodiment of administration is such that a regulatory factor is locally administered, by a method such as injection or transdermal administration, into a vicinity of a nervous system (e.g., spinal cord) to be treated.

A dose (effective amount) of the regulatory factor may be appropriately set in accordance with age or sex of a human or an animal to which the regulatory factor is to be administered, symptoms, administration routes, the number of times the regulatory factor is administered, or the like. In a case where in vivo assay with use of the regulatory factor is performed in advance according to need, it is possible to determine the dose without performing an excess experiment.

For example, in a case where the regulatory factor is a so-called low-molecular compound (e.g., 5-(N-ethyl-N-isopropyl)amiloride or an analog thereof), a preferable dose of the regulatory factor falls within a range of, for example, 0.1 mg or more but 100 mg or less, 1 mg or more but 50 mg or less, and 1 mg or more but 20 mg or less, per kilogram weight of a human or an animal. The number of times the regulatory factor is administered is not particularly limited, provided that the regulatory factor has an effect of regulating neuronal axon elongation. The number of times the regulatory factor is administered may be appropriately set in accordance with, for example, a kind of regulatory factor, the dose, administration routes, symptoms, or age or sex of a human or an animal.

A human or a non-human animal as the subject to which the regulatory factor is to be administered may be any animals, provided that the human or non-human animal has neurons, however, it is preferable to select a subject from a group of the mammals including a human. Mammals, to which the regulatory factor is to be administered are exemplified by, but not particularly limited in kind, animals such as a mouse, a rat, a rabbit, a guinea pig, and a primate other than a human; pet animals such as a dog and a cat; domestic animals such as a cow and a horse; and a human. Among these mammals, a human is particularly preferable.

Examples of a human or a non-human animal to which the regulatory factor is to be administered encompass an animal having a dysfunction of a nervous system such as damages to a nervous system (in particular, spinal cord injury); and erethism such as atopic dermatitis and pain disorder.

Further, a regulatory factor for suppressing occurrence of macropinocytosis in a growth cone and growth cone collapse is administered to a human or non-human animal that has a dysfunction of a nervous system or is to undergo an operation for treating the dysfunction. In this case, together with the regulatory factor, an attractive axon guidance molecule may also be administrated to promote neuronal axon elongation.

Meanwhile, a regulatory factor for inducing occurrence of macropinocytosis in a growth cone is administered to a human or a non-human animal having erethism, so that an undesirable neurite of a neuron is collapsed. For erethism developed in a vicinity of skin such as atopic dermatitis, it is preferable that a regulatory factor be transdermally administered by use of, for example, a patch. For erethism as pain disorder, it is preferable that a regulatory factor be locally administered to affected area by injection (for example, using an injector, or an injection pump).

Further, the scope of the present invention encompasses treating neuronal growth cone with a regulatory factor to regulate macropinocytosis caused by a repulsive axon guidance molecule in vitro. Also in case of treating neuronal growth cone with a regulatory factor to regulate macropinocytosis in vitro, the regulatory factor may be given into a system in a quantity effective in regulating neuronal axon elongation. Here, the regulatory factor may be administered alone, or may be administered as a component of a pharmaceutical composition (described later) suitable for a purpose of the administration.

In a case where the regulatory factor is a nucleic acid molecule, the regulatory factor is introduced into a neuron by use of, for example, a vector containing an expressible regulatory factor. Examples of a kind of vector encompass a plasmid vector and a virus vector (preferably, adenovirus vector, adeno-associated virus vector, retrovirus vector, and the like). Examples of a method of introducing a vector into a neuron encompass electroporation (Nucleic, Acids Res. 15, 1311-1326 (1987)), a calcium phosphate method (Mol. Cell Biol. 7, 2745-2752 (1987)), and a lipofection method (Cell 7, 1025-1037 (1994); Lamb, Nature Genetics 5, 22-30 (1993)).

Meanwhile, in a case where the regulatory factor is not a nucleic acid molecule, it may be arranged such that a regulatory factor is added to a medium in which a neuron is cultured, and then the medium is caused to contact with the neuron or is introduced into the neuron.

In either case, after the regulatory factor is given into a system in a quantity effective in regulating neuronal axon elongation, a neuron is cultured in vitro. Note that a neuron which is treated in an in-vitro system is exemplified by a primary culture cell and a cell line, but is not particularly limited in kind.

(Method of Treating Neuronal Growth Cone with Plurality of Regulatory Factors in Combination)

It is possible to use a plurality of kinds of regulatory factors in combination to treat neuronal growth cone to regulate macropinocytosis caused by a repulsive axon guidance molecule. Normally, regulatory factors that suppress macropinocytosis in a growth cone and growth cone collapse are used in combination, or regulatory factors that induce macropinocytosis in a growth cone are used in combination.

One preferable combination of the regulatory factors is 1) an inhibitor of a sodium/proton exchanger in a growth cone and 2) a factor that increases binding activity and/or amount of Syntaxin1B protein in a growth cone.

[2. Pharmaceutical Composition]

The present invention also provides a pharmaceutical composition containing the regulatory factor as component thereof. Components other than the regulatory factor which constitute the pharmaceutical composition are not particularly limited, and can be mixed with a pharmaceutically acceptable carrier, lubricant, preservative, stabilizer, humectant, emulsifier, salt for osmotic pressure adjustment, buffering agent, coloring agent, flavor, a sweetener, antioxidant, viscosity modifier, etc.

One preferable example of a pharmaceutical composition is a combined agent (neuronal axon elongation regulating agent) containing, as the regulatory factor, both 1) an inhibitor of sodium/proton exchanger in a growth cone and 2) a factor that increases binding activity and/or amount of Syntaxin1B protein in a growth cone.

The carrier which is pharmaceutically acceptable is not particularly limited, however, it is preferable that the carrier be one that has a characteristic of (A) not inhibiting a function (regulation of neuronal axon elongation) of a regulatory factor in a case where the carrier is administered together with the regulatory factor and (B) having no practically adverse effect on a human or a non-human animal to which a therapeutic agent with the carrier is to be administered.

Conventionally known carriers in this field can be widely used as the carrier. For example, such a carrier is specifically exemplified by, but not limited to water, various kinds of salt solutions, alcohols, vegetable oil, polyethylene glycol, gelatin, lactose, amylose, magnesium stearate, talc, silicic acid, paraffin, fatty acid monoglyceride, fatty acid diglyceride, hydroxymethyl cellulose, and polyvinyl pyrrolidone. A kind of carrier may be appropriately selected in accordance with a dosage form of a pharmaceutical composition, a method of administering a pharmaceutical composition, and/or the like.

The dosage form of the pharmaceutical composition is not particularly limited, and examples of the dosage form encompass a tablet, a pill, powder, a liquid medicine, a suspension, an emulsion, a granule, a capsule, a suppository, a patch, an ointment/a liniment, and an injection.

Further, in a case where the regulatory factor is a nucleic acid molecule, a pharmaceutical composition could be a gene therapy medicine. The gene therapy medicine may be administered in such a way that the regulatory factor is directly administered to a human or a non-human animal by injection, or in such a way that a vector into which the regulatory factor is incorporated is administered to a human or a non-human animal by injection. Further, the vector is not particularly limited, and examples of the vector encompass vectors applicable to a gene therapy such as an adenovirus vector, an adeno-related virus vector, an adeno-associated virus vector, a herpesvirus vector, a vaccinia virus vector, and a retrovirus vector. Note that the gene therapy medicine may be a liposomal formulation.

The nucleic acid molecule of the invention can be applied to the nucleic acid based drug. In a case of nucleic acid based drug, the drug delivery system in the public domain including atelocollagen, aromatic series cation peptide, cationic lipid and the like, is not particularly limited in kind, can be also used for the introduction in addition to the above conventional method.

It is preferable that an expression regulatory sequence to express the regulatory factor in a neuron is incorporated into the vector contained in the gene therapy medicine. Here, the expression regulatory sequence is, for example, a promoter or an enhancer.

[3. Screening Method and Production Method]

The present invention further provides a method of screening the regulatory factor that regulates macropinocytosis which is dependent on a repulsive axon guidance molecule.

This screening method includes the following steps in this order: a culturing step of culturing a neuron in the presence of a candidate of a regulatory factor; a measuring step of measuring binding activity against a target molecule which the wild type Syntaxin1B naturally binds, and/or amount of Syntaxin1B protein in a growth cone of the neuron; and a sorting step of sorting the candidate that modulates binding activity against the target molecule and/or amount of Syntaxin1B protein in the growth cone of the neuron as compared with a case where the candidate does not exist.

The culturing step can be carried out in accordance with a conventional method for culturing a neuron, except that a candidate for the regulatory factor is added into culture medium of the neuron in a system in the culturing step. In view of improving sensitivity of screening, however, it is more preferable to carry out the treating step under the colocalization of the candidate with a repulsive axon guidance molecule. For example, the repulsive axon guidance molecule is exemplified by Sema3A or ephrin-A2, but not limited in kind, and preferably Sema3A. Note that for example, the neuron is exemplified by a primary culture cell and a cell line, but not particularly limited in kind.

In the measuring step, binding activity and/or amount of Syntaxin1B protein in a growth cone of the neuron are/is measured. In order to carry out the measurement easily, it is preferable to measure the amount of Syntaxin1B protein. Note that the amount of Syntaxin1B protein may be measured by, for example, a conventional method in which (i) an amount of transcription (amount of mRNAs) of Syntaxin1B gene is indirectly grasped by quantifying the amount of transcription by, for example, realtime PCR or (ii) Syntaxin1B protein is quantified by an immunologic method.

The screening step is a step for screening a candidate for a regulatory factor by comparing, with a control, a candidate that modulated in binding activity and/or amount of Syntaxin1B protein in the growth cone of the neuron, which control is a control that has been subjected to the culturing step through the measuring step under the same conditions as those of the neuron except that the candidate was contained in the system. Here, candidates that decreased binding activity and/or amount of Syntaxin1B protein could induce macropinocytosis in a growth cone and collapse the growth cone of a neuron (neurite). Meanwhile, candidates that increased binding activity and/or amount of Syntaxin1B protein could reduce macropinocytosis in a growth cone and inhibit growth cone collapse of a neuron (neurite).

A Candidate for the regulatory factor which has been selected by the sorting step is formulated as needed, to prepare the above pharmaceutical composition (neuronal axon elongation regulating agent).

<Summary>

As described above, each invention of the present application encompasses any one of the contents below.

1) A method of regulating neuronal axon elongation, comprising: a treating step of treating neuronal growth cone with a regulatory factor to regulate macropinocytosis caused by a repulsive axon guidance molecule.

2) The method as set forth in 1), wherein the regulatory factor is an inhibitor of a sodium/proton exchanger in the growth cone.

3) The method as set forth in 2), wherein the inhibitor is 5-(N-ethyl-N-isopropyl)amiloride or an analog thereof.

4) The method as set forth in 1), the regulatory factor modulates binding activity and/or amount of Syntaxin1B protein in the growth cone.

5) The method as set forth in 4), wherein the regulatory factor increases the binding activity and/or the amount of the Syntaxin1B protein in the growth cone.

6) The method as set forth in 5), wherein the regulatory factor contains (A) a nucleic acid that encodes any one of Syntaxin1B protein and a fragment of Syntaxin1B protein or (B) any one of Syntaxin1B protein and a fragment of Syntaxin1B protein.

7) The method as set forth in 2), further comprising: an administering step of administering an effective amount of the regulatory factor to (A) a human or a non-human animal sustaining damage to a nervous system or (B) a human or a non-human animal to have an operation on a nervous system, the administering step being carried out before the treating step.

8) The method as set forth in 5), further comprising: an administering step of administering an effective amount of the regulatory factor to (A) a human or a non-human animal sustaining damage to a nervous system or (B) a human or a non-human animal to have an operation on a nervous system, the administering step being carried out before the treating step.

9) The method as set forth in 2), wherein, as the regulatory factor, the inhibitor and a regulatory factor for increasing binding activity and/or amount of Syntaxin1B protein in the growth cone are used.

10) A method of screening a regulatory factor for regulating macropinocytosis dependent on a repulsive axon guidance molecule, the method comprising: a culturing step of culturing a neuron in the presence of a candidate of a regulatory factor; a measuring step of measuring binding activity and/or amount of Syntaxin1B protein in a growth cone of the neuron; and a sorting step of sorting the candidate that modulates binding activity and/or amount of Syntaxin1B protein in the growth cone of the neuron as compared with a case where the candidate does not exist.

11) The screening method as set forth in 10), wherein the culturing step is carried out under colocalization with a repulsive axon guidance molecule.

12) A neuronal axon elongation regulating agent, comprising: an inhibitor of a sodium/proton exchanger in a growth cone; and a regulatory factor that increases binding activity and/or amount of Syntaxin1B protein in the growth cone.

EXAMPLE

The present invention will be described more specifically below on the basis of the following Example etc. It should be noted that the present invention is not limited to the Example etc. below.

[Method and Material]

<Material>

An F-12 medium (Invitrogen) or an L-15 medium was used as a culture medium. Alexa Fluor 488-labeled high-molecular-weight (10 kDa) dextran (Alexa Fluor 488-dextran) stock solution (Invitrogen) was prepared in the F-12 medium with or without neurotoxin C1.

Anti-Syx1B antibody (purchased from Synaptic Systems) was generated against synthetic peptide (sequence GKLAIFTDDIKMDSQMT: SEQ ID NO 1). This sequence of the synthetic peptide corresponds to amino acid residues 171-187 in mouse Syx1B protein. This sequence of the synthetic peptide is identical to that present in chick Syx1B protein cloned in this example. Epoxomicin was purchased from Peptide Institute, and used at final concentration of 1 µM.

Neurotoxin C1 was purified from *Clostridium botulinum* type C (Reference (Kurazono et al., 1985): Fems Microbiol Lett 30:47-51.) and used at a final concentration of 200 nM.

<Cell Culture>

Primary culture DRG neurons were prepared from embryonic day 7-9 male and female chick (*Gallus gallus*) embryos in accordance with a previous report (Reference (Kabayama et al., 1999):Neuroscience 88:999-1003.). Primary culture DRG neurons were cultured in an F-12 medium supplemented with 50 ng/ml nerve growth factor (NGF) (Calbiochem) or in an L-15 medium supplemented with 10% fetal bovine serum, 2 mM glutamine, 5 ng/ml NGF, 0.6% glucose, and gentamicin (Roche Diagnostics).

After electroporation, cells were cultured in an F-12-based medium supplemented with 1×MACS Supplement B27 PLUS (Miltenyi Biotech) or in an L-15-based medium supplemented with 1×MACS Supplement B27 PLUS.

<Endocytosis of Alexa Fluor 488-Dextran>

To visualize endocytic activity in growth cones, the cells were exposed to 0.5 mg/ml (Mr 10,000) fixable Alexa Flour 488-dextran (Invitrogen) for 90 min with 200 nM neurotoxin C1.

Images of the living growth cones were obtained after washing the growth cones three times with Alexa Flour 488-dextran-deficient balanced salt saline (BSS) imaging buffer (pH 7.4). The Alexa Flour 488-dextran-deficient BBS imaging buffer contains the following (in mM): 2 $CaCl_2$, 5.4 KCl, 115 NaCl, 10 glucose, and 20 HEPES.

To quantify the percentage of dextran-labeled growth cones, the cells were cultured in an F-12-based medium and treated with neurotoxin C1 in the presence of Alexa Fluor 488-dextran for 90 min. Then, the cells were washed three times with the Alexa Fluor 488-dextran-deficient F-12 medium, and immediately after the washing, the cells were fixed with 4% PFA.

In the experiments using siRNAs, cells transfected with siRNAs were cultured in an L-15-based medium as described previously (Reference (Kabayama et al., 1999):Neuroscience 88:999-1003.) and exposed to 0.5 mg/ml (Mr 10,000) fixable Alexa Fluor 594-dextran (Invitrogen) for 30 min at 6 h after electroporation. The cells were fixed after being washed with an Alexa Fluor 594-dextran-deficient L-15-based medium.

In the experiments using Sema3A, cells were cultured in an F-12-based medium and exposed to 0.5 mg/ml Alexa Fluor 594-dextran for 10 min in the presence of 1 µg/ml Sema3A.

The effects of macropinocytosis inhibitor ethylisopropylamiloride (EIPA) on dextran uptake, growth cone collapse, and neurite elongation were assayed by pretreating DRG neurons for 15 min with 10 µM or 100 µM EIPA before addition of dextran.

Flourescence images of Alexa Fluor 488 and Alexa Fluor 594 in the growth cone were obtained by GFP optics and Discosoma red (DsRed) optics, respectively.

The percentage of growth cones that took up dextran was calculated from a random selection in the culture. In the experiments using siRNAs, cells were cotransfected with an EGFP-expressing vector for visualization of siRNAs. The percentage of dextran-labeled growth cones was calculated from all EGFP-positive growth cones in the culture.

<Labeling of Growth Cone Vesicles>

To visualize growth cone vesicles (GCVs), the cells were exposed to 5 µg/ml Alexa Fluor 594-labeled wheat-germ agglutinin (WGA) (Invitrogen) for 10 min at 37° C. Subsequently, the cells were washed three times with a fresh medium prewarmed at 37° C. without Alexa Fluor 594-WGA and were cultured again. These cells were used for experiments involving treatment with neurotoxin C1 and Axexa Fluor 488-dextran at 60 min after the washing.

<Construction of Expression Vectors>

Full-length chick Syx1B was obtained from an embryonic day 9 chick DRG cDNA library by PCR. The primers used were 5'-GGAACAGCCATGAAGGACCGC-3' (SEQ ID NO 2) and 5'-CTATAGGCCCAAAGTGCCACAAATG-3' (SEQ ID NO 3), designed on the basis of previously identified chick Syx1B (NCBI database accession number NM205074). A nucleotide sequence of cDNA of full-length chick Syx1B obtained by PCR was registered as Syntaxin1B-2 in the DNA Data Bank of Japan database (accession number AB244720). This Syx1B was subcloned into the EcoRI site of the pEGFP-C1 vector (Clontech).

<RNAi>

Two pairs of Syx1B siRNAs (Syx1B-siRNA1 and Syx1B-siRNA2) and scrambled siRNAs (iGENE Therapeutics) were synthesized by transcription and purification by use of PAGE. The following siRNA sequences were used in this experiment.

```
(1) Syx1B-siRNA1
Sense strand (SEQ ID NO 4):
5'-r(GCUCCAAGUUGAAAGCCAUAGAGCAAG)-3'

Antisense strand (SEQ ID NO 5):
5'-r(UGCUCUAUGGCUUUCAACUUGGAGCAU)-3'

(2) Syx1B-siRNA2
Sense strand (SEQ ID NO 6):
5'-r(CCGAUGAUAUCAAAAUGGACUCGCAAG)-3'

Antisense strand (SEQ ID NO 7):
5'-r(UGCGAGUCCAUUUUGAUAUCAUCGGAU)-3'

(3) Scrambled siRNA
Sense strand (SEQ ID NO 8):
5'-r(CGAUUCGCUAGACCGGCUUCAUUGCAG)-3'

Antisense strand (SEQ ID NO 9):
5'-r(GCAAUGAAGCCGGUCUAGCGAAUCGAU)-3'
```

The concentration of those RNAs was 40 nM during electroporation.

<Mutagenesis>

An EGFP-tagged Syntaxin 1B was prepared with a 7 bp silent mutation at the targeting region of each siRNA. The EGFP-tagged Syntaxin 1B encoded the wild-type Syx1B protein sequence (SS-Syx1B).

A QuikChange Multi Site-Directed Mutagenesis kit (Stratagene) was used to generate mutations. The following primers were used (SEQ ID NO 10~11):

```
5'-r(GAAGACGGCCAACAAAGTGCGTTCCAAACTGAAGGCGATTGA
ACAGAGCATTGAGCAGGAGGAG)-3';
and 5'-r(CGGGAAGTTGGCCATCTTCACGGACGACATAAAGATGGATTCT
CAGATGACCAAGCAGGCCCTG)-3'.
```

<Electroporation>

In total, 7.5×10⁵ cells were suspended in an L-15 medium containing 10 μg of a pEGFP vector or a pEGFP-Syx1B vector and incubated on ice for 10 min.

The cells were then transferred to chilled cuvettes (Bio-Rad) and transfected with an electroporator (0.2 V, 950Ω; Bio-Rad Gene Pulser).

The cells were immediately suspended in 10 ml of a prewarmed L-15-based culture medium which is plated onto a Petri dish, were incubated for 30 min at 37° C. to remove cell debris, and then were plated on poly-L-lysine- and laminin-coated glass-bottom culture dishes.

For quantification of the knockdown efficiency of Syx1B with siRNAs, the cells were transfected with siRNAs by electroporation.

The cells were cultured in an L-15-based medium and harvested by using a scraper at 6 h after electroporation in order to be subjected to Western blot analysis.

For quantifying effects of siRNAs on macropinocytosis, growth cone collapse, and neurite elongation, the transfected cells were cultured in an L-15-based medium supplemented with MACS Supplement B27 PLUS.

In experiments involving Sema3A, the transfected cells were cultured in an F-12-based medium supplemented with MACS Supplement B27 PLUS.

<Imaging and quantitative analysis of fluorescence signals>

For time-lapse imaging under differential interference contrast (DIC) and fluorescence microscopy, growth cones that were not in contact with other cells were selected.

The growth cones were observed by using an inverted microscope (IX70; Olympus). The inverted microscope is equipped with DIC optics, GFP optics (excitation, 490 nm; dichroic mirror, 505 nm; emission, 515 nm), DsRed optics (excitation, 555 nm; emission, 620 nm), 60× objective (numerical aperture 1.25), and a xenon lamp.

The images were acquired with a cooled CCD camera (Cool SNAP HQ; Roper Scientific) driven by MetaMorph (version 7.0) imaging software (Universal Imaging Corporation). The temperature was maintained at 37° C. by perfusing the cells with prewarmed BBS buffer.

The DIC and fluorescence images were acquired continuously.

Measurements were performed by using 2×2 binning (1 pixel=0.21×0.21 μm).

The integrated intensity of the growth cone was quantified by subtracting the nonspecific background fluorescence.

<Growth Cone Collapse Assay>

Recombinant human Sema3A/Fc chimera (Sema3A; R & D Systems) and recombinant mouse ephrin A2/Fc chimera (ephrin A2; R & D Systems) were used at 1 μg/ml for the growth cone collapse assay.

Dissociated DRG neurons from embryonic day 7-9 chicks were cultured for at least 12 h in an F-12 medium (Invitrogen) containing 50 ng/ml NGF. To investigate the effect of Sema3A, the culture medium was changed to an F-12 medium containing 0.1 ng/ml NGF at 2 h before the growth cone collapse assay. Subsequently, the culture medium was changed to BSS buffer. The cells were incubated for 30 min before their use in the growth cone collapse assay. In experiments using epoxomicin, the cells were treated with 1 μM/ml epoxomicin for 15 min before the addition of 1 μM/ml Sema3A.

Growth cone collapse was quantified as the reduction in the surface area of growth cones. The growth cone area was defined as a hand-like region extending from a distal part of a neurite to a growth cone neck whose width is equal to the width of the neurite. The width of each neurite was calculated by measuring the width of the neurite region at a location that was 30 μm apart from the distal part of each neurite. This calculation was adopted because the mean length of the control growth cone was less than 30 μm. If a growth cone collapsed completely or the width of the growth cone was less than that of the each neurite, the neurite region at the location that was 30 μm apart from the distal part of the neurite was considered as the growth cone neck.

<Macropinocytosis Assay in NIH3T3 Cells>

NIH3T3 cells transfected with pEGFP or pEGFP-Syx1B were exposed to a medium containing 2.5 mg/ml of Alexa Fluor 594-dextran in the presence of serum for 30 min. Macropinocytosis in the NIH3T3 cells was quantified by measuring the integrated fluorescence intensity of internalized Alexa Fluor 594-dextran in the cells.

<Western Blot Analysis>

The proteins were extracted in a passive lysis buffer (Promega). Then, 15 μg of protein extract was subjected to 12.5% SDS-PAGE and transferred to a PVDF membrane (Millipore). The blots were blocked with 2% skimmed milk in PBS containing 0.1% Tween 20, incubated in the presence of affinity-purified rabbit anti-Syx1B (1 μg/ml; Synaptic Systems) or rabbit polyclonal anti-actin antibody (1:4000 dilution; Sigma), and incubated in the presence of HRP-labeled donkey anti-rabbit IgG (Jackson ImmunoResearch). Immunoreactive bands were visualized with an Enhanced Chemiluminescence Plus detection system (GE Healthcare).

For visualization of polyubiquitination of endogenous proteins, cells were cultured for 6 h with an L-15-based medium and pretreated with 1 μM epoxomicin 15 min before the 15 min Sema3A treatment. Total proteins were extracted with passive lysis buffer [10 nM ubiquitin aldehyde (Peptide Institute) and complete protease inhibitor cocktail (Roche)]. Polyubiquitinated proteins were analyzed by Western blot analysis using anti-ubiquitin antibody (Roche).

<Immunocytochemistry>

After Sema3A or vehicle treatment, the cells were fixed with 4% PFA for 1 h at 37° C., followed by permeabilization with 0.3% Triton X-100 in PBS for 2 min at a room temperature.

The cells were then immediately washed three times with a blocking solution (1% BSA and 0.1% Triton X-100 PBS), followed by incubation with the blocking solution for 1 h at a room temperature, and were then incubated in the presence of anti-Syx1B (0.5 μg/ml) and anti-synaptosomal-associated protein 25 (SNAP25) antibody (1:500 dilution, clone SM-81; Sternberger Monpclonals) for 2 h at a room temperature. Immunofluorescence signals were visualized by incubation with Alexa Fluor 488-labeled donkey anti-rabbit antibody (Invitrogen) and Alexa Fluor 594-labeled donkey anti-mouse antibody (Invitrogen). The integrated fluorescence intensity of Syx1B in the growth cones was normalized to that of the SNAP 25 protein.

<Statistical Analysis>

All the data are representative of at least three independent experiments. The results are expressed as the mean±SEM. The data were analyzed with the GraphPad Prism 4.0 program (Graph-Pad Software). $p<0.05$ was considered statistically significant.

[Results]

<Syx11B is a Negative Regulator of Macropinocytosis>

Figure 1:
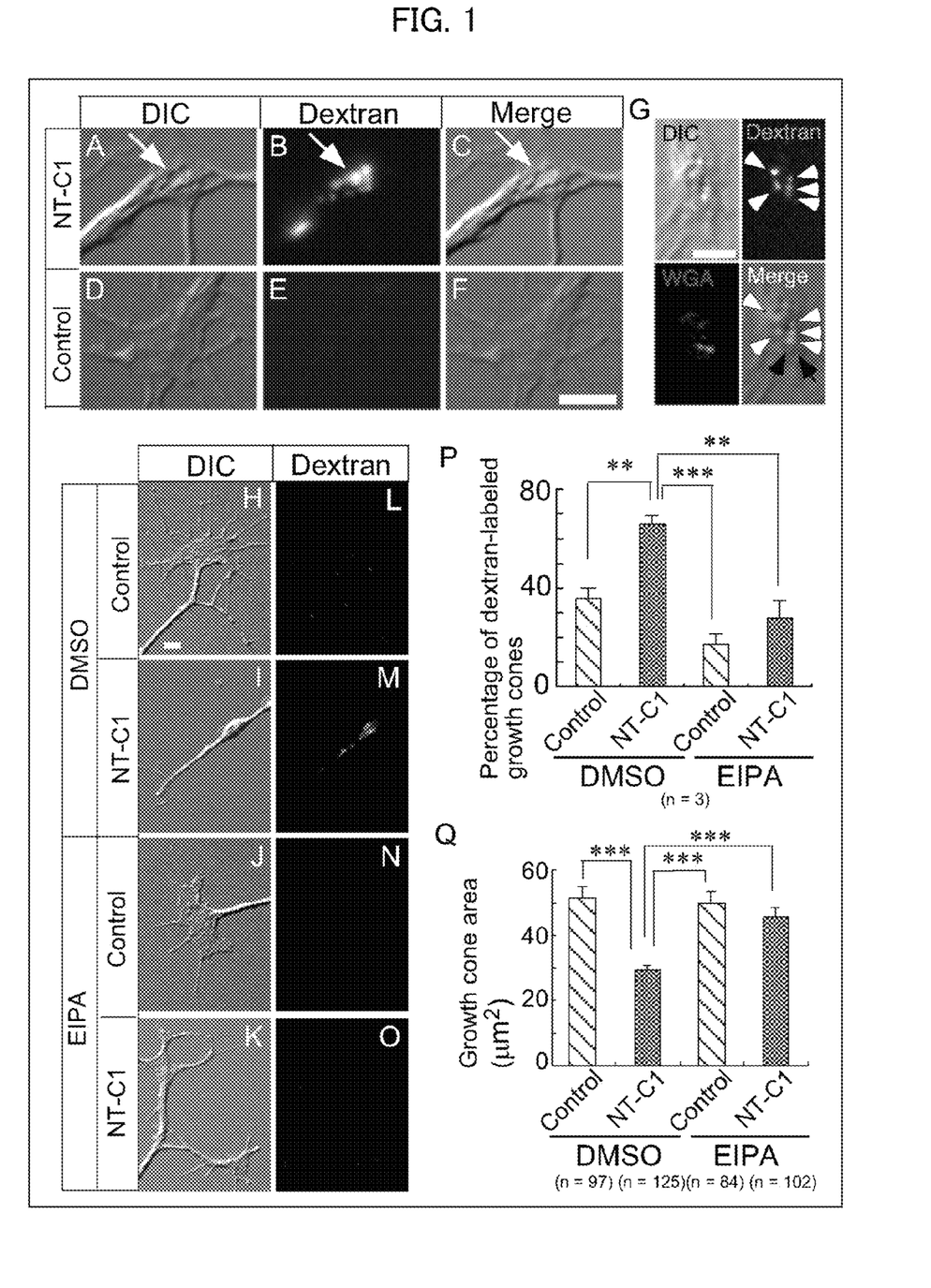
FIG. 1 is views showing results in Example of the present invention, which prove that neurotoxin C1-induced vacuoles are formed by macropinocytosis.

During 90 min neurotoxin C1 treatment, primary culture DRG neurons were exposed to an Alexa Fluor 488-dextran-containing medium. The growth cones were imaged after washing cells with Alexa Fluor 488-dextran-deficient BBS imaging buffer. Unlike the controls, neurotoxin C1-treated cells exhibited marked accumulation of Alexa Fluor 488-dextran in the DIG-identifiable vacuoles of living growth cones (FIGS. 1A-F).

The fusion of WGA-labeled small GCVs has been postulated to form neurotoxin C1-induced vacuoles (Reference: Igarashi et al., 1996_J Cell Biol 134:205-215.). However, WGA-fluorescent puncta were not colocalized with Alexa Fluor 488-dextran-positive large vacuoles in the neurotoxin C1-treated growth cones (FIG. 1G).

Although neurotoxin C1-induced large vacuoles are known to move in a retrograde manner (Reference: Igarashi et al., 1996_J Cell Biol 134:205-215.), the WGA-labeled vesicles in the neurotoxin C1-treated growth cones were not transported in this manner, indicating that the neurotoxin C1-induced vacuoles were not formed by the fusion of WGA-labeled GCVs.

Next, whether neurotoxin C1-induced endocytosis is macropinocytosis was investigated using EIPA, a macropinocytosis-specific inhibitor. Neurotoxin C1-induced uptake of Alexa Fluor 594-dextran (FIG. 1H, I, L, M, P) and reduction in growth cone surface area (FIG. 1H, I, Q) were blocked by 15 min pretreatment with 100 μM EIPA (FIG. 1J, K, N-Q). These results indicate that neurotoxin C1-induced large vacuoles are formed by macropinocytosis and not the fusion of WGA-labeled vesicles.

Note that FIG. 1 is views showing that neurotoxin C1-induced vacuoles are formed by macropinocytosis. FIGS. 1A-F show DIC, fluorescence, and merged images of a living growth cone in the presence of Alexa Fluor 488-dextran, A-C show DIC, fluorescence, and merged images treated with neurotoxin C1, and D-F show DIC, fluorescence, and merged images of a control buffer. The arrows in FIG. 1 indicate large vacuoles which were colocalized with Alexa Fluor 488-dextran.

FIG. 1G shows that WGA-labeled GCVs were not colocalized with neurotoxin C1-induced large vacuoles. More specifically, a DIC image of a living growth cone treated with neurotoxin C1, fluorescence images of Alexa Fluor 488-dextran (green) and Alexa Fluor 594-WGA (red), and merged images of the DIC image and the fluorescence images. The white arrowheads indicate Alexa Fluor 488-dextran localized to large vacuoles and the black arrows indicate Alexa Fluor 594-WGA fluorescent puncta.

FIGS. 1H-O show DIC images and fluorescence images of a fixed growth cone treated with a control buffer (H, L, J, N) or neurotoxin C1 (I, M, K, O). FIG. 1H, I, L, and M each show an experiment in the presence of DMSO, FIG. 1J, N, K, and O each show an experiment in the presence of 100 μM EIPA.

FIG. 1P shows the percentage of growth cones labeled with Alexa Fluor 594-dextran during 90 min neurotoxin C1 or control buffer treatment in the presence of DMSO or 100 μM EIPA ($p<0.01$, *$p<0.001$, two-tailed non-repeated-measures ANOVA followed by Newman-Keuls post hoc multiple comparison test.).

FIG. 1Q shows a growth cone area treated with neurotoxin C1 or a control buffer in the presence of DMSO or 100 μM EIPA (***$p<0.01$, two-tailed non-repeated-measures ANOVA followed by Newman-Keuls post hoc multiple comparison test.). The error bars (in P and Q) indicate SEM. The scale bar indicates 5 μm.

siRNAs for Syx1B (Syx1-siRNAs) was used to investigate whether knockdown of this molecule caused macropinocytosis, growth cone collapse, and reduced neurite elongation. The endogenous Syx1B level normalized to actin protein in Syx1-siRNA-transfected DRG neurons was significantly reduced to $53.4\pm3.1\%$ ($p<0.0001$, two-tailed unpaired t test) as compared with control siRNA-transfected DRG neurons (FIG. 2A).

Figure 2:
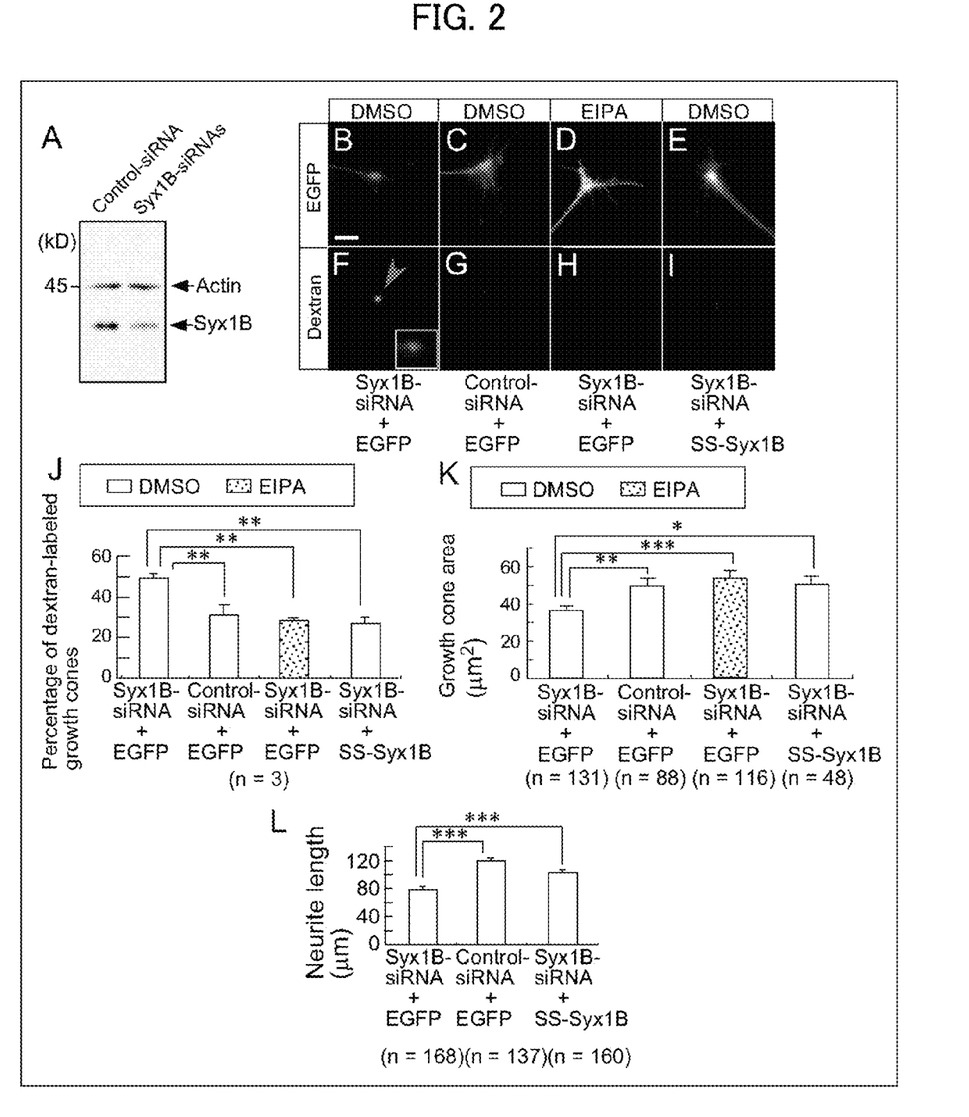
FIG. 2 is views showing results in Example of the present invention, which prove that Syx1B (Syntaxin1B) is a negative regulator of macropinocytosis in growth cones.

Syx1B-siRNA-transfected cells exhibited strong accumulation of Alexa Fluor 594-dextran in growth cones (FIG. 2B, F, J), growth cone collapse (FIG. 2B, K), and reduced neurite elongation (FIG. 2L) under physiological conditions, whereas control siRNA-transfected growth cones exhibited no such effect (FIG. 2C, G, J-L). These Syx1B knockdown-mediated phenotypes were reversed by 15 min pretreatment with 10 μM EIPA (FIG. 2D, H, J-L).

Because siRNA-induced RNA interference in mammalian systems may have off-target effects (Reference: Jackson et al., 2003_Nat Biotechnol 21:635-637.), whether Syx1B-siRNA-induced phenotypes can be suppressed by reintroducing Syx1B into DRG neurons was investigated.

An EGFP-tagged syntaxin 1B with a 7 bp silent mutation at the siRNA-targeting region, which encoded the wild-type Syx1B protein sequence (SS-Syx1B), was prepared. As predicted, SS-Syx1B was expressed in growth cones cotransfected with Syx1B-siRNA (FIG. 2E). SS-Syx1B expression suppressed Syx1B-siRNA-induced uptake of Alexa Fluor 594-dextran (FIG. 2I, J), growth cone collapse (FIG. 2E, K), and reduced neurite elongation (FIG. 2L). Furthermore, Syx1B overexpression inhibited macropinocytosis in NIH3T3 cells (not shown).

Note that FIG. 2 is views showing that Syx1B is a negative regulator of macropinocytosis in growth cones. FIG. 2A shows a result of Western blot analysis of endogenous Syx1B expression level in DRG neurons transfected with Syx1B-siRNA or control siRNAs.

FIGS. 2B-I show fluorescence EGFP (top, white) and Alexa Fluor 594-dextran (bottom, white) fluorescence images of a fixed growth cone cotransfected with the indicated siRNAs and EGFP or EGFP-labeled SS-Syx1B in the presence of DMSO or 10 μM EIPA. The blue arrowheads indicate incorporated Alexa Fluor 594-dextran. The insert in FIG. 2F is an enlargement of a merged image of EGFP (B, green) and dextran (F, magenta).

FIG. 2J shows the percentage of siRNA-transfected growth cones labeled with Alexa Fluor 594-dextran under the various conditions shown in FIGS. 2B-I. FIG. 2K shows a growth cone area of siRNA-transfected growth cones shown in FIGS. 2B-I. FIG. 2L shows a neurite length of siRNA-transfected cells shown in FIG. 2B, C, and E. *$p<0.05$, $p<0.01$, *$p<0.001$ (two-tailed non-repeated-measures ANOVA followed by Newman-Keuls post hoc multiple comparison test.). The error bars (FIGS. 2J-L) show SEM. The scale bar indicates 10 μm.

<Sema3A Signaling Decreases Syx1B Protein Level>

Figure 3:
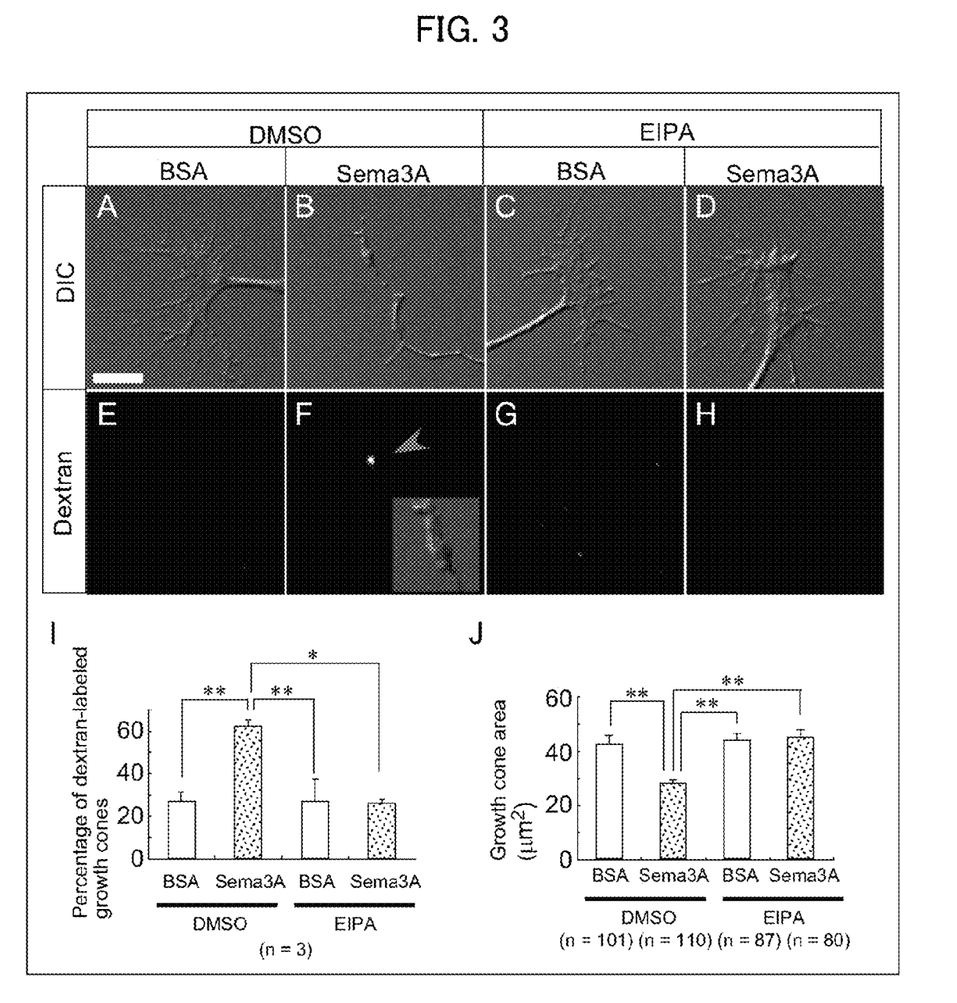
FIG. 3 is views showing results in Example of the present invention, which prove that macropinocytosis is required for Sema3A-induced growth cone collapse.

Sema3A-induced uptake of Alexa Flour 594-dextran (FIG. 3A, B, E, F, I) and growth cone collapse (FIG. 3B, J) were suppressed by 15 min pretreatment of cells with 10 μM EIPA (FIG. 3C, D, G, H-J).

These results indicated that macropinocytosis was required for Sema3A-induced growth cone collapse and raised the possibility that Sema3A-induced macropinocytosis was mediated by the suppression of Syx1B, because Syx1B-reduction-triggered macropinocytosis was required for growth cone collapse (see FIG. 2).

Figure 4:
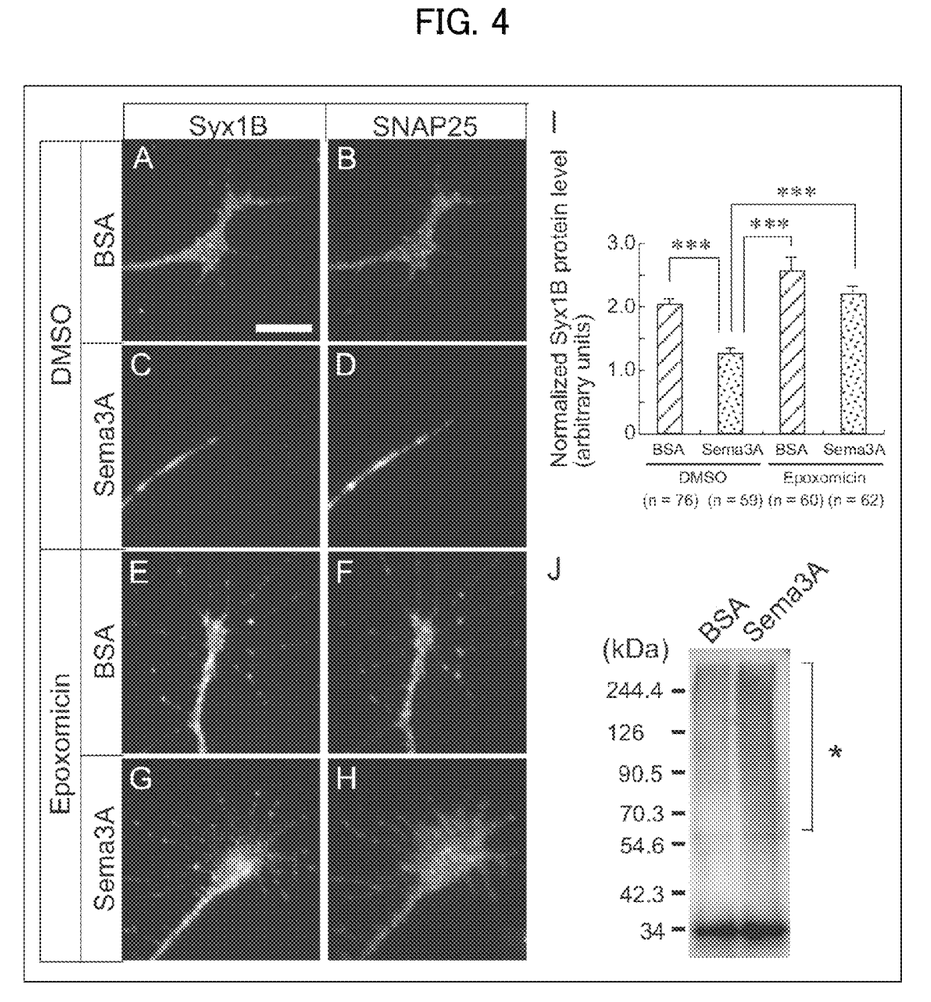
FIG. 4 is views showing that Sema3A decreases Syx1B protein in Example of the present invention.

To examine the possibility, the effect of Sema3A on Syx1B expression in growth cones was investigated. Immunocytochemistry revealed that the protein level of Syx1B in growth cones was reduced by 10 min Sema3A treatment (FIG. 4A, C, I). The protein level of Syx1B normalized to that of SNAP25 (FIG. 4B, D) in the growth cones was significantly reduced by 10 min Sema3A treatment (FIG. 4I).

This rapid suppression of Syx1B suggested that the protein is degraded by the proteasome. To test this, cells were exposed to a medium containing 1 μM epoxomicin, a specific proteasome inhibitor. As a result of the above epoxomicin treatment, Sema3A-induced suppression was suppressed (FIGS. 4E-H, I).

When Western blot analysis with anti-ubiquitin antibody was performed using cell lysate prepared from cells treated with Sema3A in the presence of 1 μM epoxomicin, a broad band with high molecular weight was increased in response to Sema3A (FIG. 4J). These results indicate that Sema3A activates the ubiquitin-proteasome pathway.

The cells were treated for 10 min with the PI3K inhibitor LY294002 [2-(4-morpholinyl)-8-phenyl-1 (4H)-benzopyran-4-one] and the effect of the PI3K inhibitor on syx1B protein expression was then evaluated. The protein level of Syx1B normalized to that of SNAP25 in the growth cones was significantly reduced by 10 min LY294002 treatment (FIG. 5A).

Figure 5:
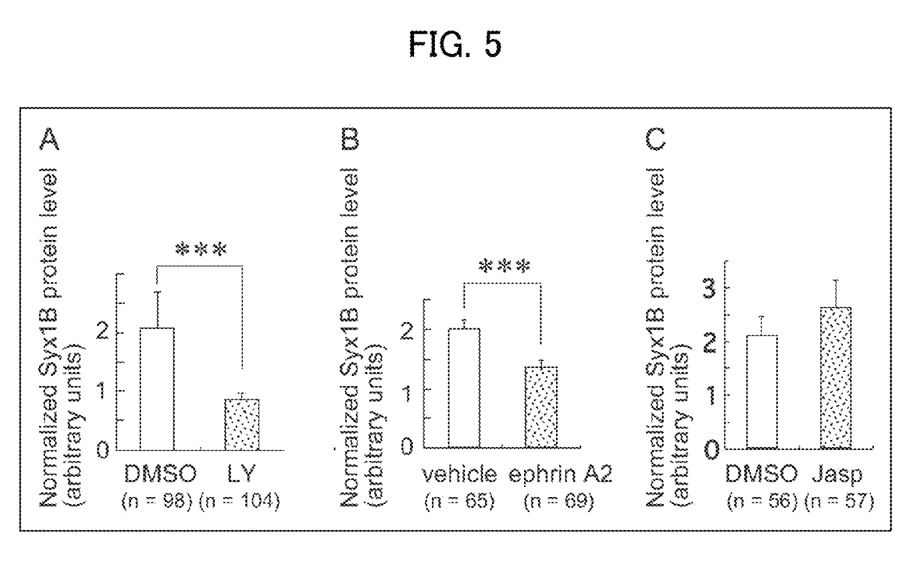
FIG. 5 is views showing that, in Example of the present invention, a Syx1B protein level in a growth cone is decreased by suppression of PI3K and ephrin A2 but not by Jasp.

Expression of Syx1B normalized to SNAP25 was decreased by 10 min treatment with ephrin A2 (FIG. 5B). In contrast, expression of Syx1B normalized to SNAP25 was not decreased in growth cones treated with jasplakinolide (Jasp), an inhibitor of F-actin depolymerization (FIG. 5C). Note that jasplakinolide (Jasp) induces growth cone collapse-like morphological changes.

These results indicate that reduction of Syx1B protein levels is not secondary to the morphological changes in growth cones during growth cone collapse. Together, these results suggest that Sema3A-PI3K signaling decreases Syx1B protein in growth cones, thereby inducing macropinocytosis.

Note that FIG. 3 is views showing that macropinocytosis is required for Sema3A-induced growth cone collapse. FIGS. 3A-H show DIC images and fluorescence images of growth cones subjected to 10 min treatment with BSA (A, C, E, G) or Sema3A (B, D, F, H) in the presence of DMSO (A, B, E, F) or 10 μM EIPA (C, D, G, H). The blue arrowheads indicate incorporated Alexa Fluor 594-dextran. The insert in FIG. 3F is an enlargement of a merged image of DIC (FIG. 3B) and dextran (FIG. 3F, magenta). FIG. 3I shows the percentage of growth cones labeled with Alexa Fluor 594-dextran under the indicated conditions shown in FIGS. 3A-H. FIG. 3J shows a growth cone area of growth cones shown in FIGS. 3A-H. *$p<0.05$, **$p<0.01$ (two-tailed non-repeated-measures ANOVA followed by Newman-Keuls post hoc multiple comparison test). The error bars indicate SEM. The scale bar indicates 10 μm.

FIG. 4 is views showing that Sema3A decreases Syx1B protein. FIGS. 4A-H show immunofluorescence images of endogenous Syx1B (A, C, E, G) and SNAP25 (B, D, F, H) in growth cones treated with BSA (A, B, E, F) or Sema3A (C, D, G, H) for 10 min in the presence of DMSO (A-D) or epoxomicin (E-H). FIG. 4I shows a relative amount of endogenous Syx1B protein normalized to SNAP25 in the growth cones (***$p<0.001$, two-tailed non-repeated-measures ANOVA followed by Newman-Keuls post hoc multiple comparison test.). FIG. 4J shows Poly-ubiquitination of endogenous proteins by Sema3A treatment in the presence of epoxomicin. Cell lysate was prepared from cells treated for min with Sema3A or BSA in the presence of 1 μM epoxomicin, immunoblotted with anti-ubiquitin antibody to detect ubiquitinated proteins as smear bands. Asterisk indicates Poly-ubiquitinated proteins. The error bars indicate SEM. The scale bar indicates 10 μm.

FIG. 5 is views showing that the Syx1B protein level in a growth cone is decreased by the suppression of PI3K and ephrin A2 but by Jasp. FIGS. 5A-C show a relative amount of endogenous Syx1B protein normalized to SNAP25, in the growth cones treated with LY294002 (LY, FIG. 5A), ephrin A2 (FIG. 5B), and Jasp (FIG. 5C). Note that the treatment of the growth cones with each drug is carried out for 10 min. ***$p<0.001$ (unpaired t test). The error bars indicate SEM. The scale bar indicates 10 μm.

<Syx1B Couples Macropinocytosis to Sema3A-Induced Growth Cone Collapse>

Figure 6:
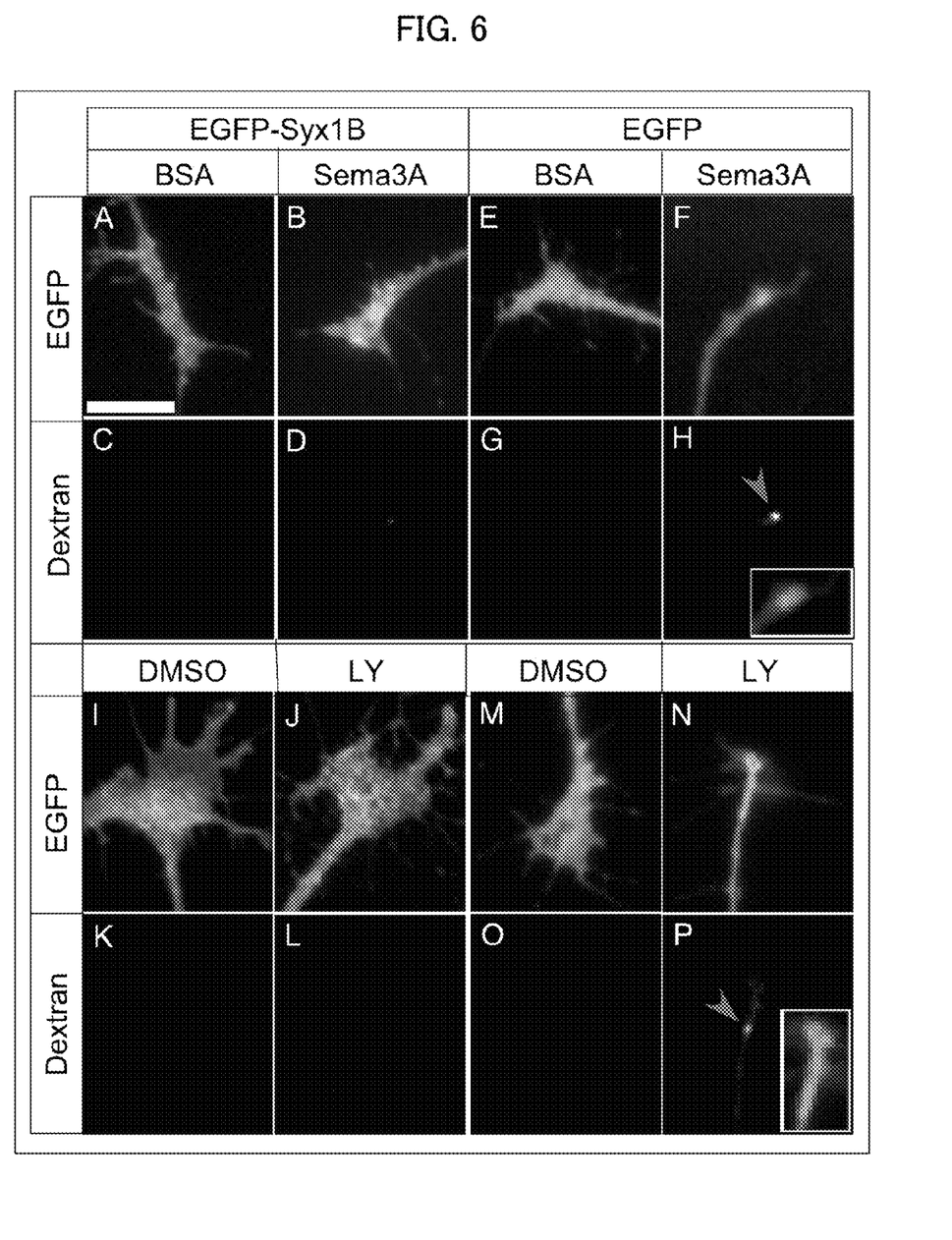
FIG. 6 is views showing effects of overexpression of EGFP-Syx1B on Sema3A- or LY294002 (LY)-induced macropinocytosis and growth cone collapse in Example of the present invention.
Figure 7:
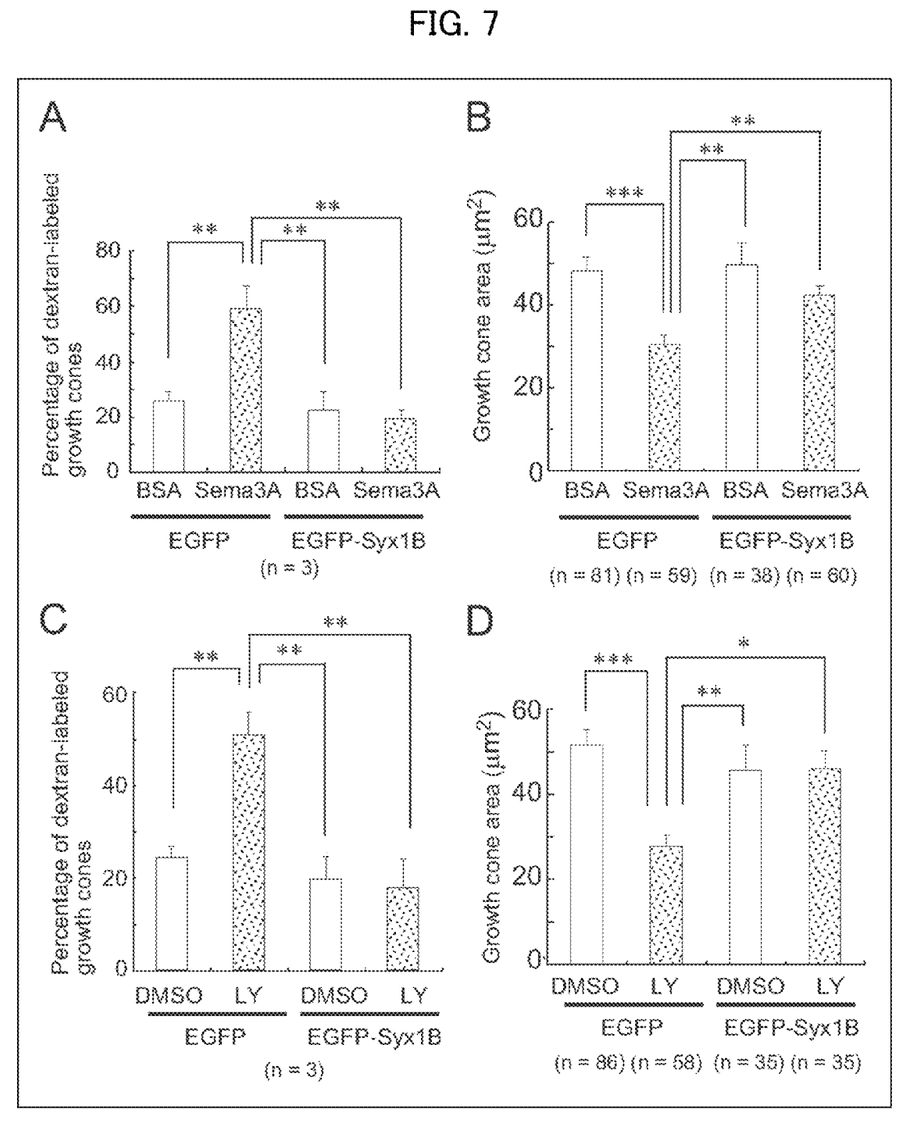
FIG. 7 is views showing that overexpression of EGFP-Syx1B suppresses Sema3A- or LY294002 (LY)-induced macropinocytosis and growth cone collapse in Example of the present invention.

A gain-of-function analysis was next performed by maintaining Syx1B expression at high levels after Sema3A treatment in the overexpression experiment. The overexpression of EGFP-Syx1B reduced Sema3A- or LY294002-induced macropinocytosis in the growth cones (FIG. 6A-D, I-L and FIG. 7A, C), and reversed the Sema3A- or LY294002-induced reduction in growth cone area (FIG. 6A-D, I-L and FIG. 7B, D), whereas the overexpression of EGFP alone had no such effect (FIGS. 6E-H, M-P and FIG. 7A-D).

Figure 8:
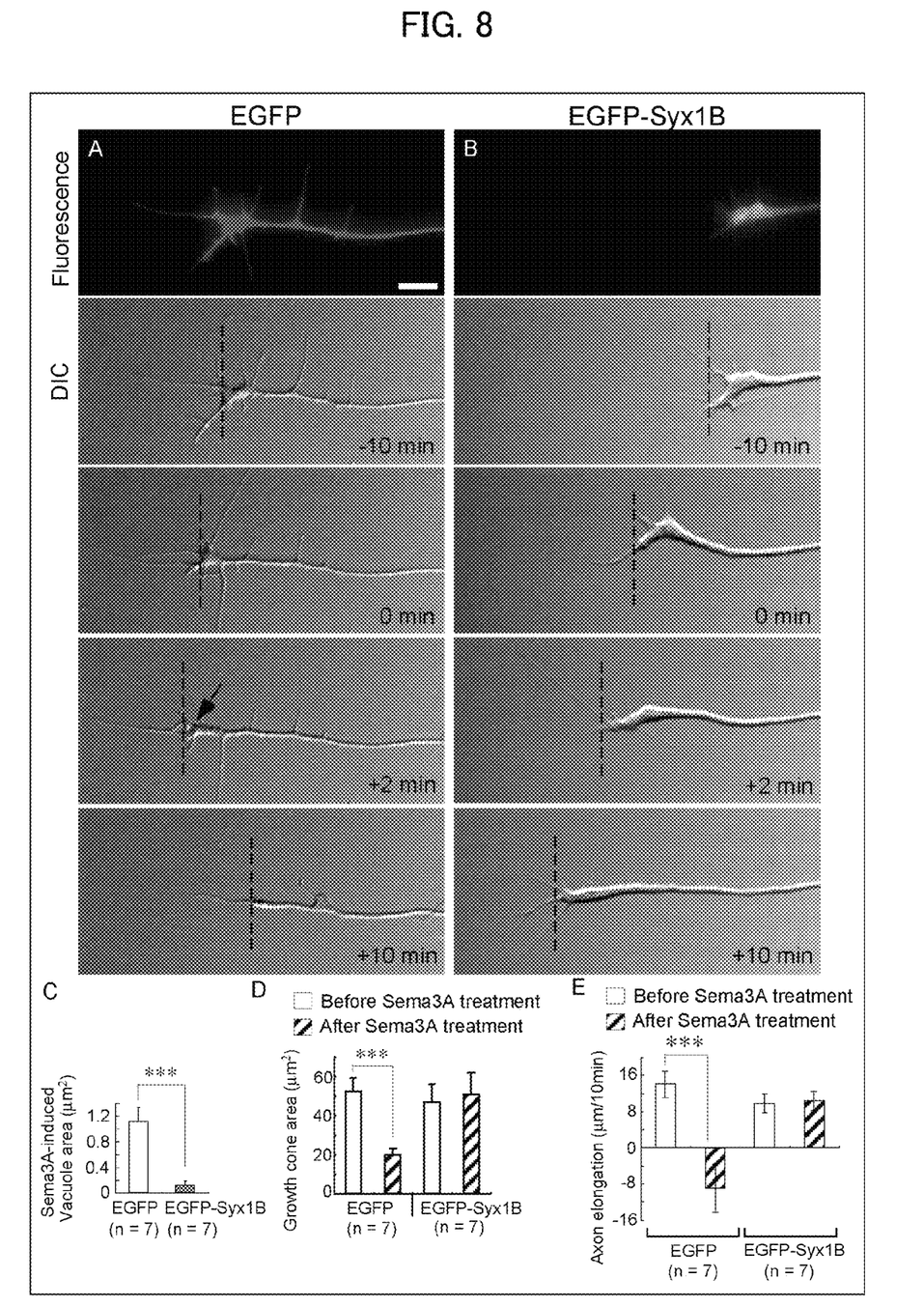
FIG. 8 is views showing how overexpression of EGFP-tagged Syntaxin1B protein (EGFP-Syx1B) affected (A) Sema3A-induced macropinocytosis and (B) prevention of neuronal axon elongation in Example of the present invention.

As illustrated in FIGS. 8A-C, the overexpression of EGFP-Syx1B reduced Sema3A-induced macropinocytosis in growth cones, however, the overexpression of EGFP alone had no such effect. Further, the overexpression of EGFP-Syx1B suppressed both reduction in areas of Sema3A-induced growth cones (FIG. 8A, B, D) and retraction of Sema3A-induced neurite (FIG. 8A, B, E). This indicates that syntaxin 1B-reduction-triggered macropinocytosis is one process of causing inhibition of Sema3A-dependent axon elongation including growth cone collapse and axon retraction.

Note that the experiment, whose results are shown in FIG. 8, was carrried out as in the case of the above <Growth cone collapse assay> using Sema3A. pEGFP or pEGFP-syntaxin1B was introduced into cells by electroporation, and the cells were cultured in an F-12 medium and were subjected to a Sema3A treatment. Then, a vacuole obtained after the Sema3A treatment, an area of a growth cone, and a neurite elongation rate were measured by time-lapse imaging. An area of the vacuole was obtained by quantifying a maximum value obtained during 10 min after Sema3A was added to the vacuole. An area of a growth cone was quantified at 0 (zero) min and 10 min after Sema3A was added. A neurite elongation rate was obtained by quantifying a length obtained before the Sema3A treatment and a length obtained at 10 min after the Sema3A treatment, and then comparing the lengths. All data were obtained from GFP-positive cells.

Note that FIG. 6 is views showing effects of overexpression of EGFP-Syx1B on Sema3A- or LY294002 (LY)-induced macropinocytosis and growth cone collapse. FIGS. 6A-P show fluorescence images of pEGFP- or pEGFP-Syx1B-transfected growth cones subjected to 10 min treatment with BSA (FIG. 6A, C, E, G), Sema3A (FIG. 6B, D, F, H), DMSO (FIG. 6I, K, M, O), or LY (FIG. 6J, L, N, P) in the presence of Alexa Fluor 594-dextran. Top panels show green fluorescence of EGFP or EGFP-Syx1B-expressing growth cones. Bottom panels show Alexa Fluor 594-dextran incorporated into growth cones. The inserts in H and P show a merged image of EGFP (FIG. 6F, green) and dextran (FIG. 6H, magenta) and a merged image of EGFP (FIG. 6N, green) and dextran (P, magenta), respectively. The scale bar indicates 10 μm.

FIG. 7 is views showing that overexpression of EGFP-Syx1B suppresses Sema3A- or LY294002 (LY)-induced macropinocytosis and growth cone collapse. FIG. 7 shows the percentage of growth cones labeled with Alexa Fluor 594-dextran (FIG. 7A, C) and growth cone area (FIG. 7B, D) of EGFP- or EGFP-Syx1B-transfected growth cones subjected to 10 min treatment with BSA, Sema3A, DMSO, or LY294002 in the presence of Alexa Fluor 594-dextran.

*p<0.05, p<0.01, *p<0.001 (two-tailed non-repeated-measures ANOVA followed by Newman-Keuls post hoc multiple comparison test.). The error bars indicate SEM.

FIG. 8 is views showing, in Example of the present invention, effects of overexpression of EGFP-tagged Syntaxin1B protein (EGFP-Syx1B) on (A) Sema3A-induced macropinocytosis and (B) inhibition of neuronal axon elongation. FIG. 8A shows a series of time-lapse images of a pEGFP-transfected growth cone (control), and FIG. 8B shows a series of time-lapse images of a pEGFP-Syx1B-transfected growth cone. Sema3A was added into a medium immediately after the experiment was started (at 0 min). The arrow in FIG. 8A indicates a vacuole obtained at 2 min after the experiment was started. The broken line in FIG. 8A indicates a leading edge of a growth cone. FIG. 8C indicates a maximum area of a vacuole in a growth cone of a pEGFP- or pEGFP-Syx1B-transfected DRG neuron subjected to the Sema3A treatment for 10 min. *P<0.001, two-tailed unpaired t-test. FIGS. 8D and 8E show (i) a change in area of a growth cone and (ii) a change in neurite elongation rate, respectively, the changes (i) and (ii) each being induced by Sema3A. *P<0.001, two-tailed paired t-test. The error bars in FIG. 8C, D, and E indicate SEM. The scale bar indicates 10 μm.

The present invention is not limited to the description of the embodiments above, and can be modified in numerous ways by a skilled person as long as such modification falls within the scope of the claims. An embodiment derived from a proper combination of technical means disclosed in different embodiments is also encompassed in the technical scope of the present invention.

All cited references cited in this specification are incorporated into the specification by referring the cited references as if disclosed matters of such cited references were described in the specification.

INDUSTRIAL APPLICABILITY

The present invention can provide a novel method of regulating neuronal axon elongation etc.

The invention claimed is:

1. A method of increasing neuronal axon elongation, comprising:

a treating step of treating neuronal growth cone with a regulatory factor to reduce macropinocytosis caused by a repulsive axon guidance molecule, the treating step inducing promotion of the axon elongation as a result of reducing the macropinocytosis, wherein the regulatory factor contains a nucleic acid that encodes for Syntaxin 1B protein, wherein the treating step comprises an administering step of administering an effective amount of the regulatory factor to a human or non-human animal, wherein the human or non-human animal is one suffering damage to a nervous system thereof or is to undergo an operation on its nervous system thereof, and wherein the regulatory factor is administered by a method comprising direct injection into a vicinity of a nervous system to be treated.

2. The method as set forth in claim 1, wherein the regulatory factor is incorporated into a vector into which an expression regulatory sequence to specifically express the regulatory factor in a neuron is incorporated.

* * * * *

SEQUENCE LISTING

```
<160> NUMBER OF SEQ ID NOS: 11

<210> SEQ ID NO 1
<211> LENGTH: 17
<212> TYPE: PRT
<213> ORGANISM: Artificial Sequence
<220> FEATURE:
<223> OTHER INFORMATION: Synthetic peptide

<400> SEQUENCE: 1

Gly Lys Leu Ala Ile Phe Thr Asp Asp Ile Lys Met Asp Ser Gln Met
1               5                   10                  15

Thr

<210> SEQ ID NO 2
<211> LENGTH: 21
<212> TYPE: DNA
<213> ORGANISM: Artificial Sequence
<220> FEATURE:
<223> OTHER INFORMATION: primer sequence

<400> SEQUENCE: 2
ggaacagcca tgaaggaccg c                                                  21

<210> SEQ ID NO 3
<211> LENGTH: 25
<212> TYPE: DNA
<213> ORGANISM: Artificial Sequence
<220> FEATURE:
<223> OTHER INFORMATION: primer sequence

<400> SEQUENCE: 3
ctataggccc aaagtgccac aaatg                                              25

<210> SEQ ID NO 4
<211> LENGTH: 27
<212> TYPE: RNA
<213> ORGANISM: Artificial Sequence
<220> FEATURE:
<223> OTHER INFORMATION: siRNA sequence

<400> SEQUENCE: 4
gcuccaaguu gaaagccaua gagcaag                                            27
```

```
<210> SEQ ID NO 5
<211> LENGTH: 27
<212> TYPE: RNA
<213> ORGANISM: Artificial Sequence
<220> FEATURE:
<223> OTHER INFORMATION: siRNA sequence

<400> SEQUENCE: 5
ugcucuaugg cuuucaacuu ggagcau                                          27

<210> SEQ ID NO 6
<211> LENGTH: 27
<212> TYPE: RNA
<213> ORGANISM: Artificial Sequence
<220> FEATURE:
<223> OTHER INFORMATION: siRNA sequence

<400> SEQUENCE: 6
ccgaugauau caaaauggac ucgcaag                                          27

<210> SEQ ID NO 7
<211> LENGTH: 27
<212> TYPE: RNA
<213> ORGANISM: Artificial Sequence
<220> FEATURE:
<223> OTHER INFORMATION: siRNA sequence

<400> SEQUENCE: 7
ugcgagucca uuuugauauc aucggau                                          27

<210> SEQ ID NO 8
<211> LENGTH: 27
<212> TYPE: RNA
<213> ORGANISM: Artificial Sequence
<220> FEATURE:
<223> OTHER INFORMATION: siRNA sequence

<400> SEQUENCE: 8
cgauucgcua gaccggcuuc auugcag                                          27

<210> SEQ ID NO 9
<211> LENGTH: 27
<212> TYPE: RNA
<213> ORGANISM: Artificial Sequence
<220> FEATURE:
<223> OTHER INFORMATION: siRNA sequence

<400> SEQUENCE: 9
gcaaugaagc cggucuagcg aaucgau                                          27

<210> SEQ ID NO 10
<211> LENGTH: 64
<212> TYPE: DNA
<213> ORGANISM: Artificial Sequence
<220> FEATURE:
<223> OTHER INFORMATION: primer sequence

<400> SEQUENCE: 10
gaagacggcc aacaaagtgc gttccaaact gaaggcgatt gaacagagca ttgagcagga      60
ggag                                                                  64

<210> SEQ ID NO 11
<211> LENGTH: 64
<212> TYPE: DNA
<213> ORGANISM: Artificial Sequence
```

-continued

```
<220> FEATURE:
<223> OTHER INFORMATION: primer sequence

<400> SEQUENCE: 11
cgggaagttg gccatcttca cggacgacat aaagatggat tctcagatga ccaagcaggc    60
cctg                                                                 64
```